United States Patent [19]

Schulte

[11] Patent Number: 4,962,024

[45] Date of Patent: * Oct. 9, 1990

[54] SIGNAL ENHANCEMENT IN ASSAY FOR AN ENZYME

[75] Inventor: Thomas H. Schulte, Cary, N.C.

[73] Assignee: Becton, Dickinson and Company, Franklin Lakes, N.J.

[ * ] Notice: The portion of the term of this patent subsequent to May 30, 2006 has been disclaimed.

[21] Appl. No.: 230,933

[22] Filed: Aug. 11, 1988

[51] Int. Cl.$^5$ ............................ C12Q 1/54; C12Q 1/48
[52] U.S. Cl. ............................................. 435/14; 435/4; 435/18; 435/19; 435/20; 435/21; 435/22; 435/23; 435/24; 435/25
[58] Field of Search .................... 435/4, 14, 26, 15–25, 435/810

[56] References Cited

U.S. PATENT DOCUMENTS

| | | | |
|---|---|---|---|
| 3,852,157 | 12/1974 | Rubenstein et al. | 435/25 |
| 4,134,792 | 1/1979 | Boyuslaski | 435/18 |
| 4,318,986 | 3/1982 | Richardson et al. | 435/24 |
| 4,409,140 | 10/1983 | Smith et al. | 435/24 |
| 4,446,231 | 5/1984 | Self | 435/4 |
| 4,463,040 | 7/1984 | Harris | 435/23 |
| 4,472,499 | 9/1984 | McCroskey | 435/4 |
| 4,492,751 | 1/1985 | Boyuslaski | 435/7 |
| 4,521,511 | 6/1985 | Stout | 435/28 |
| 4,835,099 | 5/1989 | Mize et al. | 435/7 |

OTHER PUBLICATIONS

Walsh, Suicide Substrates: Mechanism–Based Enzyme Inactivators, 1982, Tetsahedron, vol. 38, No. 7, pp. 871–909.
Gelb et al., Fluoro Ketone Inhibitors of Hydrolytic Enzymes, Apr. 9, 1985, Biochemistry, vol. 24, No. 8, pp. 1813–1817.

*Primary Examiner*—Sam Rosen
*Attorney, Agent, or Firm*—Richard E. Brown

[57] ABSTRACT

A method for assay for an unknown enzyme suspected to be present in a liquid includes signal amplification by use of a second enzyme and a blocked modulator for the second enzyme. Unknown enzyme in the liquid removes a blocking group from the blocked modulator. The resulting modulator activates or inhibits the second enzyme which catalyzes an indicator reaction in which a substrate is converted to a product. The presence or absence of the unknown enzyme in the liquid is indicated by a signal, such as a color change or a rate of color change, associated with the indicator reaction. The concentration of the enzyme in the sample may be determined by the measurement of the signal. The invention includes a kit of materials useful for performing the method of the invention. The method involves the hydrolyzing of a blocked fluoroketone inhibitor to facilitate the analytical method.

20 Claims, 1 Drawing Sheet

SIGNAL ENHANCEMENT IN ASSAY FOR AN ENZYME

1. FIELD OF THE INVENTION

This invention relates to assay of an enzyme and materials used therein, and more particularly relates to a method and materials for assay in which enhancement of a detectable signal is achieved by modulation of enzymatic catalysts of an indicator reaction.

2. BACKGROUND OF THE INVENTION

Although the science of enzymes is almost 100 years old and the key roles that enzymes play in many biochemical reactions were understood 40 years ago, the applications of enzymology to clinical diagnosis are much more recent. As recently as 20 years ago these applications accounted for only about 3-5% of the total number of tests performed in the clinical laboratory, and only four or five enzymes were routinely assayed.

Today, in contrast, enzyme assays may account for as much as 25% of the total work load in larger hospital laboratories, and as many as 20-25 enzymes may be routinely assayed. Detailed procedures for these routine assays may be found in any standard textbook on clinical or diagnostic chemistry.

In an enzyme assay, enzyme concentration in a body fluid, such as serum, urine and cerebrospinal fluid, is determined to be either within a normal range or outside of the normal range. In some assays, an abnormal enzyme concentration is the result of a bacterial or viral infection, and assay for a specific enzyme is diagnostic for a specific pathogen. In other cases, mere detection of an enzyme not normally present in a fluid, such as serum, may be indicative of tissue or organ damage. For example, detection in plasma of alcohol dehydrogenase, which is liver specific, and acid phosphatase, which is prostate specific, pinpoints tissue damage in these organs. Measurement of alkaline phosphatase activity has importance in diagnosing hepatobiliary and bone disorders.

Enzyme assays depend on enzyme catalysis of conversion of a substrate to a product which may be detected or measured. If the concentration of the substrate in an enzyme reaction is gradually increased, keeping all other factors constant, the rate of reaction will increase with increasing substrate concentration until a maximum value is reached. Any further increase in substrate concentration will elicit no further increase in reaction rate. Thus, when the substrate is present in sufficient excess, the rate of reaction depends only on enzyme concentration.

Since enzymes are true catalysts and are not changed during the reaction, the rate of an enzyme reaction, in the presence of sufficient substrate, is constant with time and is dependent only on the concentration of enzyme in the assay system. If the enzyme to be analyzed is present in low concentration, the reaction rate will be very low, and a long period of time may be required in order for sufficient product for detection to form. This is a severe disadvantage in those cases where speed of detection is of the essence, as, for example, in determining the presence of a pathogen in blood or urine.

Another limitation in enzyme analysis is the frequent presence in clinical samples of substances which decrease assay sensitivity by interfering with enzyme activity. These substances, generally referred to as interferences, are particularly troublesome in analysis of enzymes in serum and urine samples. Interferences have conventionally been dealt with by diluting the sample to the point where the interference no longer occurs. This dilution, however, may reduce the enzyme concentration in the sample to the point where it is no longer detectable.

Assay sensitivity in immunoassay has been increased by various amplification procedures. In cascade amplification, the number of detectable (generally colored) molecules is increased by use of two or more enzymes or enzyme derivatives. U.S. Pat. No. 4,463,090 to Harris discloses a cascade amplification immunoassay in which a large molecule activator, such as an enzyme or a proenzyme coupled to a ligand, activates a second enzyme which reacts with a substrate to product a detectable signal or in turn activates a third enzyme.

U.S. Pat. No. 4,446,231 to Self discloses a cycling amplification enzyme immunoassay which includes primary and secondary enzyme systems and a modulator for the second enzyme system. The primary system includes a first enzyme coupled to a ligand. In a first embodiment of the Self invention, the first enzyme system acts on a modulator precursor to liberate a modulator. The modulator is a cofactor of the secondary enzyme which activates the second enzyme system to catalyze the reaction of a substrate to a detectable product. During the reaction, the modulator is converted to an inactive form, and cycling is accomplished by a third enzyme which reactivates the modulator. In a second embodiment the modulator is an inhibitor of the secondary system, and is removed by the primary enzyme system whereby the secondary system is activated to act on the substrate and thereby produce the detectable product. Column 37 of Self discloses use of the patented method for detection of an enzyme.

Boguslaski et al., U.S. Pat. No. 4,492,751 teaches a cycling system in which an enzyme substrate or coenzyme in conjugated to one member of the specifically binding pair.

A variety of molecules has been shown to cause specific inactivation of a target enzyme. A subset of inhibitors, termed mechanism-based inhibitors, are substrates for enzymes which react with an enzyme to form a covalent bond. Mechanism-based inhibitors have been reviewed by Walsh (Tetrahedron 38, 871 (1982)). Another subset of inhibitors includes molecules which act as stable transition-state analogs. Gelb et al. have disclosed some fluoroketones as transition-state inhibitors of hydrolytic enzymes in Biochemistry 24, 1813 (1985).

Enzyme assays are valuable additions to the list of analytical techniques; however, they are subject to the above-described limitations. It is toward improved enzyme assays which solve these problems that this invention is directed.

SUMMARY OF THE INVENTION

One aspect of the present invention is a method for assay of an enzyme, hereinafter referred to as the unknown enzyme, in a liquid. The liquid suspected of containing the unknown enzyme is combines with a blocked modulator and a second enzyme. The unknown enzyme removes the blocking group to provide a modulator for the second enzyme. A substrate for the second enzyme is then added. The substrate is converted by the second enzyme to a product which provides a detectable signal, the conversion of the substrate to the product by the second enzyme being modulated by the modulator. The substrate-to-product reaction is hereinafter referred to as the indicator reaction.

The preferred blocked modulator of the present invention is a blocked inhibitor which is converted by the unknown enzyme to an inhibitor. The preferred second enzyme is an esterase, and the preferred substrate is a chromogen which is convertible by the esterase to a product of a different color. Most preferably, the chromogen is colorless and is converted to a colored product by the esterase, the conversation of chromogen to product being inhibited by the inhibitor.

Another aspect of the invention includes a kit of materials for performing the method of the invention substantially as described above.

In any assay system which includes unblocking of an enzyme inhibitor, severe constraints are placed on both the inhibitor and the blocked inhibitor if the assay is to achieve maximum sensitivity. In accordance with the present invention, the blocked inhibitor is an excellent substrate for the unknown enzyme, but is essentially unreactive toward the second enzyme. Likewise, the unblocked inhibitor is a potent inhibitor of the second enzyme, but has essentially no effect on the unknown enzyme. Because the reactions of the blocked inhibitor and inhibitor with the unknown and second enzymes respectively are highly selective, "short circuits" characteristic of prior art cycling EIA systems due to cross reactivities are substantially eliminated.

Thus, the invention provides a versatile method for assay for enzymes present in very low concentration in a liquid. The method enhances assay sensitivity up to 100 fold thereby providing many advantages over conventional enzyme assays. Enzymes present at much lower concentrations may be determined. Interferences may be overcome without sample dilution, which would further reduce already very low enzyme concentration. The time required to perform the assay is greatly reduced allowing more assays to be carried out by a clinical laboratory in a given time. Often, the signal can be read with the naked eye, eliminating a need for expensive and cumbersome equipment. Significant savings in cost and space are thereby achieved, enabling assays in accordance with the invention to be carried out in small clinical laboratories or even in a physician's office.

DETAILED DESCRIPTION OF THE PREFERRED EMBODIMENTS

Figure 1:
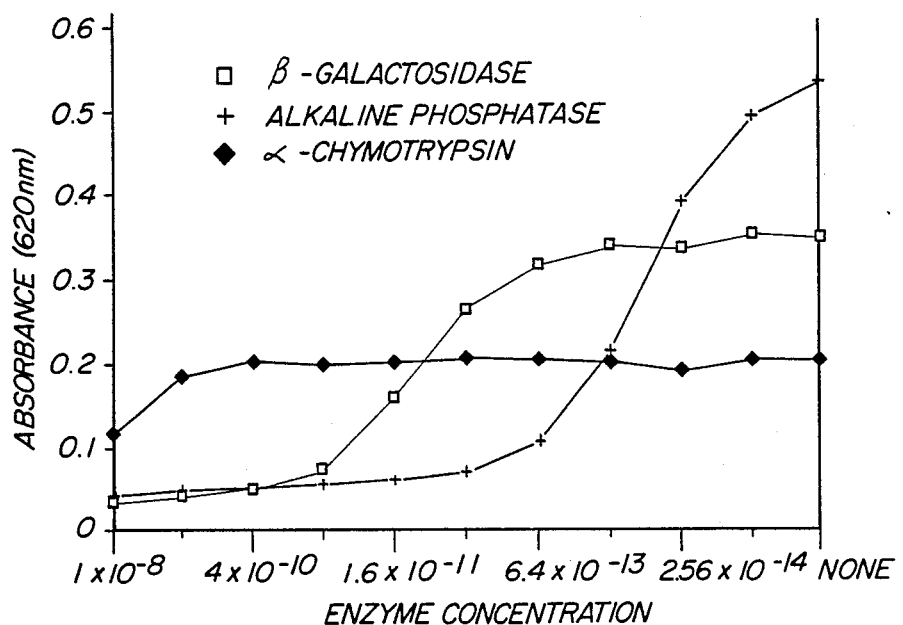
FIG. 1 depicts the results of typical enzyme assays in accordance with the method and materials of the invention.

While this invention is satisfied by embodiments in many different forms, there is described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the method of the invention, an unknown enzyme suspected to be present in a liquid may be determined by an assay method which includes at least two amplification stages. In this disclosure, the term "determined" means either detection of the enzyme, i.e., its presence or absence, or measurement of its concentration in the liquid.

A first amplification stage in unblocking of the modulator for the second enzyme by the unknown enzyme. A second amplification stage is catalysis of the indicator reaction by the second enzyme. These amplification steps take place sequentially to provide signal amplification of 100 fold or higher whereby an enzyme present in the sample may often be detected with the naked eye. If additional amplification is desired, additional enzymes may be provided which participate in a cascade of sequential reactions wherein any one or all of the reactions may provide further signal amplification.

The preferred assay method of the invention will first be described with reference to the assay flow sheet below to provide a general understanding of the assay components and their interaction, after which each component will be discussed in detail.

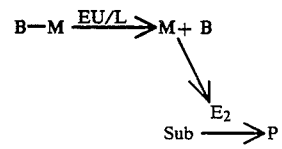

In the above flow sheet, the following definitions apply, wherein a hyphen indicates a chemical bond, a solid arrow indicates a chemical conversion and the dotted arrow indicates modulation of the second enzyme and thereby modulation of the indicator reaction.

L—liquid to be assayed
EU—unknown enzyme
$E_2$—second enzyme
B-M—blocked modulator
M—free modulator for second enzyme
B—blocking group for modulator
Sub—substrate
P—product It is seen from the flow sheet that the liquid suspected of containing the unknown enzyme is combined with the blocked modulator and the second enzyme. Any unknown enzyme present in the liquid removes the blocking group and liberates free modulator. A substrate for the second enzyme is added and is converted in the indicator reaction to a detectable product by the second enzyme, the catalytic activity of the second enzyme being modulated by the free modulator. The level of product is either directly or inversely proportional to the level of free modulator, and thus to the concentration of unknown enzyme, depending on whether the modulator is an activator or inhibitor respectively. The actual signal measured may be a color associated with the indicator reaction, as, for example, the color of the product or rate of formation thereof, or the color of the substrate or the rate of disappearance thereof.

Turning now to a detailed description of the assay components, the unknown enzyme may be from any source. For example, it may be present in a body fluid, or it may be isolated from a body fluid and subsequently introduced into a different liquid, such as buffer. In other cases, the unknown enzyme may be from a source other than a body fluid, as, for example, a culture of microorganisms or a cellular extract thereof. On the other hand, the unknown enzyme may not be from a living source, for example, it may be a synthetic enzyme.

Any enzyme which can remove a blocking group from a blocked modulator for a second enzyme may be determined by the method of the invention. Preferred unknown enzymes are generally hydrolases, such as phosphatases, sulphatases, amidases proteases, $\beta$-lactamases, esterases, glycosidases and the like. Specific examples of suitable unknown enzymes which may be determined by the method of the invention are trypsin, pepsin, $\alpha$-chymotrypsin ($\alpha$-C), thrombin, mammalian liver esterase, acetylcholinesterase, $\beta$-galactosidase ($\beta$-gal), $\beta$-glucuronidase, alkaline phosphatase (AP), acid phosphatase, penicillinase and leucine aminopeptidase.

The blocked modulator may be any material which may be converted by the known enzyme to a modulator of the second enzyme. The preferred blocked modulator has two components, the modulator and the blocking group. The most preferred blocked modulator is a blocked inhibitor which is unreactive toward the second enzyme until its blocking group is removed by the unknown enzyme and the inhibitor is liberated into the assay medium. Thus, the choice of the components of the blocked inhibitor depends on the unknown enzyme and the second enzyme to be used. The blocking group should be one which can be covalently conjugated to the inhibitor by a bond which can be cleaved substantially selectively by the unknown enzyme, and the inhibitor component should inhibit the activity of the second enzyme while having substantially no effect on the unknown enzyme. The blocking group, after cleavage from the blocked inhibitor, should be substantially innocuous toward all other assay components. Thus, the nature of the second enzyme and its substrate will be discussed prior to further description of the blocked inhibitor and the inhibitor.

In the assay of the invention, the second enzyme is generally a hydrolase which converts the substrate to the product. Suitable hydrolases are, for example, phosphatases, peptidases such as trypsin, chymotrypsin and pepsin, or preferably esterases such as acetyl cholinesterase (AChE) and butyl cholinesterase. The most preferred second enzyme is a carboxyesterase, such as rabbit liver esterase (RLE).

The substrate may be any substance containing a group which may be cleaved in the indicator reaction by the second enzyme to provide a product detectable by a signal associated with color. Thus, in one embodiment of the invention, the signal detected is the development or disappearance of a color, or a change from one color to another. In another embodiment of the invention the signal may be a change in the rate at which the substrate is converted to the product, for example, the color of a substrate may be observed to remain unchanged for a specified length of time. Preferably, the signal is measured at a predetermined time after the addition of the substrate. The elapsed time may be from about 0.1 to 60 min., preferably about 1 to 10 min. If desired, a stop reagent may be added to stop the indicator reaction at the predetermined time so that the signal can be measured at a later time. Measurement may be made either instrumentally or, preferably, with the naked eye.

It is preferred that the substrate be colorless until cleaved by the second enzyme to give a colored product. Suitable substrates are indoxyl esters and, preferably, esters of nitrophenols, such as ortho and para nitrophenyl acetates or butyrates. These substrates are colorless until cleavage of the acetyl or butyryl groups by carboxyesterase occurs to give colored nitrophenols. Thus, when the modulator is an inhibitor and the substrate is an ester of a nitrophenol, the signal which is measured is inhibition of color formation.

It is evident that fluorimetry may be used in the method of the invention. In this embodiment of the invention, the second enzyme may convert a fluorogen to a fluorophore wherein the signal measured is modulation of fluorescence. For this embodiment of the invention, it is preferred that the modulator be an inhibitor and the second enzyme be an esterase.

As mentioned above, the unknown enzyme cleaves the blocking group from the blocked inhibitor to provide the inhibitor of the second enzyme. Suitable enzyme inhibitors and blocked enzyme inhibitors are shown in general formulas I–IV, set forth below, wherein the nature of group B, as described later, determines whether the compound is an inhibitor or a blocked inhibitor:

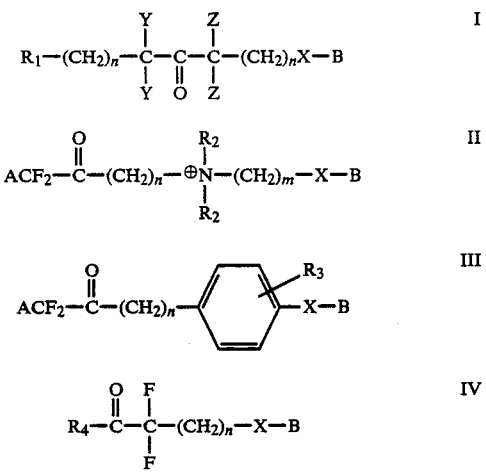

In formulas I–IV, $R_1$ may be H, lower alkyl of 1–6 carbon atoms, branched or unbranched, phenyl, benzyl, phenyloxy, benzyloxy or

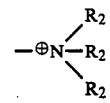

wherein $R_2$ may be lower alkyl of 1–6 carbon atoms; $R_3$ may be H, nitro, alkoxy, halogen and the like; $R_4$ may be an alkyl group of 1–10 carbon atoms or an alkenyl or alkynyl group of 2–10 carbon atoms optionally substituted with an aryl group or an aryl group substituted with a nitro, hydroxyl, mercapto, alkoxy, haloalkyl, hydroxyalkyl, mercaptoalkyl group; Y and Z may independently be H of R wherein at least one of Y and Z is F; X may be O, S or $NR_5$ wherein $R_5$ may be H or $R_2$; n may be 1–6; m may be 2–6; A may be F or $CF_3$; and B may be H, a phosphoric acid or salt, a glycosyl group, an amino acid residue, such as a lysine or arginine residue covalently conjugated to X through the amino acid carboxyl group, an acyl group of 2–4 carbon atoms such as an acetyl or butyryl group, or a peptide of the formula:

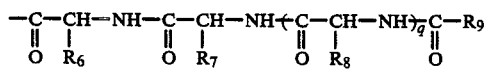

wherein $R_6$ is $(CH_2)_4NH_2$, wherein P is bonded to X and n may be as described above.

The inhibitor and blocked inhibitor in accordance with formulas I to IV may be synthesized by any sequence of conventional chemical reactions as may be envisioned by one skilled in the art. Suitable and convenient methods are given in the Examples, below. The following list of effective enzyme inhibitors is intended to be exemplary only.

| | Name | nmr data | Ki (M)* (Esterase) |
|---|---|---|---|
| 1. | 1,1,1-trifluoro-3-(4-hydroxy-phenyl)propanone | (CDCl3)- 3.91(s,2H), 5.21(bs,1H), 6.90(d,2H), 7.10(d,2H) | $2.0 \times 10^{-6}$, RLE |
| 2. | 1,1,1-trifluoro-3-(3-hydroxy-phenyl)-2-propanone | (CDCl3)- 4.00(s,2H),(4.80(bs,1H), 6.80(m,3H), 7.30(m,1H) | $>10^{-4}$, PLE |
| 3. | 1,1,1-trifluoro-4-(4-hydroxy-phenyl)-2-butanone | (CDCl3)- 2.95(m,4H), 4.90(bs,1HY), 6.92(dd,4H)J = 4.60Hz | $2.0 \times 10^{-8}$, RLE |
| 4. | 1,1,1-trifluoro-4-(3-hydroxy-phenyl)-2-butanone | (CDCl3)- 2.94(t,2H), 3.05(t,2H), 5.70(bs,1H), 6.80(m,3H), 7.15(m,1H) | $1.0 \times 10^{-7}$, RLE |
| 5. | 1,1,1-trifluoro-5-(4-hydroxy-phenyl)-2-pentanone | (CDCl3)- 1.91(t,2H), 2.59(t,2H), 2.68(t,2H), 5.23(bs,1H), 6.95(d,2H), 7.10(d,2H) | $1.0 \times 10^{-8}$, RLE |
| 6. | 1,1,1-trifluoro-5-(3-hydroxy-phenyl)-2-pentanone | (CDCl3)- 1.95(p,2H), 2.70(t,2H), 2.95(t,2H), 5.40(bs,1H), 6.70(m,3H), 7.30(m,1H) | $1.7 \times 10^{-7}$, RLE |
| 7. | 1,1,1-trifluoro-6-(4-hydroxy-phenyl)-2-hexanone | (CDCl3)- 1.63(m,4H), 2.59(q,2H), 2.70(q,2H), 5.55(bs,1H), 6.77(d,2H) 7.02(d,2H) | $2.0 \times 10^{-8}$, RLE |
| 8. | 1-phenyl-3,3-difluoro-10-hydroxy-4-decanone | (CDCl3)- 1.35(m,4H), 1.65(m,4H), 2.25(m,2H), 2.70(q,2H), 2.75(t,2H), 3.15(bs,1H), 3.55(t,2H), 7.25(m,5H) | |
| 9. | 1,1,1-trifluoro-5-hydroxy-2-pentanone | (CDCl3)- 2.15(m,4H), 4.03(bs,1H), 4.2(m,2H) | $3.0 \times 10^{-4}$, PLE |
| 10. | 1,1,1-trifluoro-6-hydroxy-2-hexanone | (CDCl3)- 1.85(m,4H), 2.10(bs,1H), 2.30(m,4H) | $4.0 \times 10^{-7}$, PLE |
| 11. | 1,1,1-trifluoro-8-hydroxy-2-octanone | (CDCl3)- 1.30-1.80(m,8H), 2.40 (bs,1H), 2.75(t,2H), 3.65(m,2H) | — |
| 12. | 1-hydroxy-5,5-difluoro-8,8-dimethyl-4-nonanone | (CDCl3)- 0.95(s,9H), 1.45(t,2H) 2.00(m,6H), 3.12(bs,1H), 4.15(m,2H) | $1.2 \times 10^{-6}$, PLE |
| 13. | 1,1,1,2,2-pentafluoro-5-(4-hydroxy-phenyl)-3-pentanone | (CDCl3)- 2.94(m,2H), 3.04(m,2H), 6.90(d,2H), 7.10(m,2H) | $8.0 \times 10^{-7}$, RLE |
| 14. | 1,1,1-trifluoro-4-(3-hydroxy-phenyl)-3-trans-buten-2-one | (CDCl3)- 5.90(bs,1H), 6.90(d,1H) j = 16Hz, 7.25(m,4H), 7.95(d,1H) j = 16Hz | $1.6 \times 10^{-7}$, RLE |
| 15. | N,N-dimethyl-N-[dimethyl-N-2-(hydrox-y)ethyl 2-(hydroxy)ethyl] 5,5,5-trifluoro-4-oxopentanaminium, hydroxide salt | (D20)- 1.90(m,4H), 3.13(s,6H), 3.30(m,2H), 3.48(m,2H), 4.01(bs,2H). | $5.0 \times 10^{-9}$, AChE |
| 16. | N,N-dimethyl-N-[4-(hydroxy)butyl] 5,5,5-trifluoro-4-oxopentanaminium, hydroxide salt | (D20)- 1.95(m,4H), 2.54(m,4H) 3.10(s,6H), 3.35(m,2H), 3.55(m,2H), 5.25(bs,1H) | $6.5 \times 10^{-8}$, ACHE |

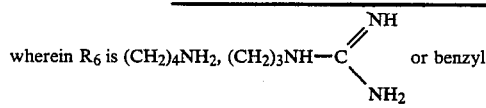

wherein $R_6$ is $(CH_2)_4NH_2$, $(CH_2)_3NH-C(=NH)NH_2$ or benzyl $R_7$ may be H or lower alkyl of 1 to 6 carbon atoms, branched or unbranched; $R_8$ may be H, lower alkyl or hydroxy-lower alkyl of 1 to 4 carbon atoms, branched or unbranched, $CH_2COOH$ or $(CH_2)_2COOH$; $R_9$ may be lower alkyl or lower alkoxy of 1 to 4 carbon atoms; branched or unbranched, phenyl, or benzyloxy; and q may be 0-10.

When B is H, formulas I to IV represent enzyme inhibitors. When B is any group other than H, formulas I to IV represent blocked enzyme inhibitors. When B is a phosphoric acid or salt thereof, it is intended that B have the formula:

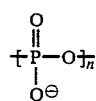

In a specific application of the invention, the unknown enzyme is alkaline phosphatase, the second enzyme is RLE or AChE and the blocked inhibitor is the fluorinated ketone of formula V. If alkaline phosphatase is present in the unknown liquid, it causes cleavage of the phosphate ester bond of V to give inhibitor of formula VI. The assay is completed by addition of o-nitrophenylbutyrate or o-nitrophenylacetate, VII.

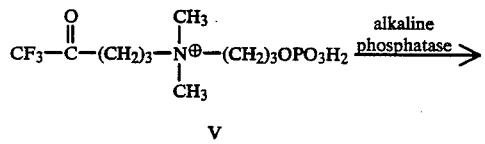

V

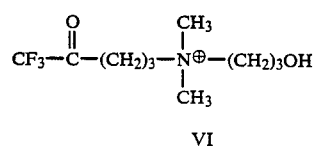

VI

-continued $$\text{VII: } o\text{-}(O\text{-}C(=O)\text{-}CH_3)\text{-}C_6H_4\text{-}NO_2 \xrightarrow{\text{RLE or AChE}} \text{VIII: } o\text{-}OH\text{-}C_6H_4\text{-}NO_2$$

VII          VIII

If inhibitor VI formed due to the presence of alkaline phosphatase in the unknown fluid, the activity of the esterase is inhibited, and colorless substrate VII is not converted to colored product VIII. If no alkaline phosphatase is present in the unknown fluid, no inhibitor VI is formed and colored product VIII therefore is formed because the esterase is not inhibited.

Thus far, two stages of enzyme amplification have been described. If additional signal amplification is desired, a multistage cascade amplification assay may be carried out wherein a plurality of reagents in the assay medium react sequentially leading ultimately to signal enhancement. In describing this embodiment of the invention, it is convenient to consider the unknown enzyme described above as a primary enzyme which enzymatically converts a reagent in the assay medium to a secondary enzyme which unblocks the modulator for the above-described second enzyme. Further, the secondary enzyme, or any subsequent enzyme, may react with additional reagents to provide additional enzymes which may continue the cascade of enzymatic reactions until the modulator is unblocked. Alternatively, the second enzyme, instead of catalyzing the indicator reaction directly, may convert a reagent in the assay medium to a third enzyme which is the catalyst for the indicator reaction. By proper selection of reagents to be added to the assay medium, any desired number of amplification stages may be carried out.

Amplification occurs in any embodiment of the invention heretofore described because the unknown enzyme, the second enzyme or any other enzyme, acts as a true catalyst wherein a single enzyme molecule may act on an essentially unlimited number of blocked modulator or substrate molecules respectively without being consumed. Thus, in theory, one molecule of second enzyme would be sufficient to detect the unknown enzyme by the method of the invention. In practice, determination of the amounts of the second enzyme, substrate and blocked modulator to be added and the number of amplification stages to be used depend on the level of amplification desired and are well within the purview of one of ordinary skill in the art.

It is evident that an almost unlimited number of assay configurations can be envisioned which are suitable for determination of the unknown enzyme. Enzyme concentration may be determined by comparing the magnitude of the signal generated by the unknown enzyme with the magnitude of the signal measured upon assay of a range of predetermined quantities of the unknown enzyme assayed under essentially identical conditions. When the method of the invention is to be used for determination of enzyme concentration, it is advantageous to read signal intensity by an appropriate instrument, such as a spectrophotometer, for example, a Beckman DU7 Spectrophotometer, Beckman Instruments, Inc., Irvine, Calif.

Another aspect of the invention is a reagent kit or package of materials for performing an assay for an unknown enzyme in accordance with the method of the invention. The kit may include a second enzyme, a blocked modulator for the second enzyme and a substrate for the second enzyme. The kit may also include standards for the unknown enzyme, as, for example, one or more samples of predetermined concentration, or it may include other enzymes and enzyme substrates useful in carrying out the assay. It may include solutions, such as saline or buffers. The components of the kit may be supplied in separate containers, as, for example, vials, or two or more of the components may be combined in a single container.

EXPERIMENTAL

Routine Analytical Techniques—Flash Silica gel chromatography was performed on ICN silica gel 32–63 mesh at 3–7 psi. Analytical TLC was performed on 0.25 mm 5×20 cm aluminum-backed silica gel plates from EM Scientific. Preparative TLC was performed on 2.0 mm 20×20 cm glass-back silica gel plates from EM Scientific. Melting points were performed on a Thomas Hoover capillary melting point apparatus and are uncorrected. NMR spectra were recorded on an IBM WP-200SY spectrophotometer and chemical shifts are reported in ppm relative to trimethylsilane. HPLC was performed on a Waters 510 two pump system with UV detection using one of two solvent systems on a Brownlee AX300 7×250 mm column; System A) initial hold for 5 minutes at 30 mM NH4OAc pH 6.5 followed by a linear gradient to 2.0 M NH4OAc over a 30 minute period followed by a hold at 1.0 M NH4OAc for 5 minutes. System B) used an isocratic buffer system of 30 mM NH4OAc pH 6.5 for 40 minutes. Flow rates were 1.0 mL/minute. Gas chromatography was performed on a H.P. 5840A Gas Chromatograph equipped with a FID and an automatic injector using a 30 M DB-1 Megabore column purchased from J&W Scientific, Inc. GC conditions were as follows; a three minute hold at 100° C. followed by a 10° C./minute gradient to 250° C. followed by a 3.0 minute hold at 250° C. at 16.0 mL/minute flow rate.

Inhibition constants were measured in 50 mM Tris pH=8.0. Enzyme and inhibitor were incubated at ambient temperature for 20 minutes. Substrate for the enzyme was then added and the rate of hydrolysis was followed spectrophotometrically. The substrate for PLE and RLE was o-nitrophenylbutyrate and for AChE was acetyl thiocholine and Ellman's reagent.

EXAMPLE I

Diammonium [4-(3-oxo-4,4,4-trifluorobutyl)phenyl]phosphate

A. Ethyl 3-(4-methoxyphenyl)-2-(1-oxo-2,2,2-trifluoroethyl)propionate

A 1 L four neck round bottom flask, fitted with reflux condenser, dropping funnel, argon inlet, and magnetic stirrer was charged with 7.17 g (0.149 M) of a 50% oil dispersion of sodium hydride and 300 mL of dry ethyl ether. Nine mL of absolute ethanol was slowly added to the stirring solution. After the evolution of hydrogen stopped, a mixture of 25 g (0.136 M) of ethyl 4,4,4-trifluoromethyl acetoacetate and 21.3 g (0.136 M) of 4-methoxybenzyl chloride was added over a 1 hour period. The mixture was then heated at reflux overnight. The reaction mixture was then cooled, extracted with water, 1 N HCl, dried (anhydrous MgSO4), and solvent removed under reduced pressure. The crude reaction mixture, 33.5 g, was chromatographed on a 60×300 mm silica gel column with a 1:3 ethyl acetate: hexane mixture. Similar fractions were combined and gave 9.0 g (27%) of the desired product as an oil. nmr(CDCl3)—α2.12(m,3H), 2.67(m,2H), 3.85(m,3H), 3.90(s,3H), 7.24(q,4H).

B. 1,1,1-Trifluoro-4-(4-hydroxyphenyl)-2-butanone

A 100 mL round bottom flask, fitted with reflux condenser, magnetic stirrer and argon inlet was charged with 2.05 g(6.7 mM) of ethyl 3-(4-methoxyphenyl)-2-(1-oxo-2,2,2-trifluoroethyl) propionate, 20 mL of 31% HBr in AcOH, and 10 mL of water. This mixture was heated overnight at 120° C., concentrated under reduced pressure and partitioned between dichloromethane and water. The organic layer was extracted with aqueous bisulfite, saturated sodium bicarbonate, dried (anhydrous MgSO4), and the solvent removed under reduced pressure. The crude reaction mixture was chromatographed on a 50×300 mm silica gel column with 1:1 ethyl acetate: hexane. Similar fractions were combined and solvent was removed under reduced pressure to yield 600 mg(41%) of product as a clear oil. nmr(CDCl3)—α2.95(m,4H), 4.90(bd,1H), 6.93(dd,4H)J=4,60 Hz.

C. Diethyl [4-(3-oxo-4,4,4-trifluorobutyl)phenyl]phosphate

A 10 mL one neck round bottom flask, fitted with argon inlet and magnetic stirrer was placed in an ice bath and charged with 400 mg (1.8 mM) of 1, 1, 1-trifluoro-4-(4-hydroxyphenyl)-2-butanone, 400 mg (2.4 mM) of diethyl chlorophosphate, 0.15 mL of dry pyridine and 5mL of dichloromethane at 5° C. The mixture was stirred overnight at ambient temperature, filtered to remove pyridine HCl, extracted with 0.2 N HCl, extracted with water, and dried (anhydrous MgSO4). Solvent removal under reduced pressure gave a crude yield of 600 mg of a brown oil. Preparative TLC using 1:1 ethyl acetate:hexane gave 600 mg(92%) of a clear oil nmr (CDCl3)—α1.50(m,6H), 3.0(m,4H), 4.20(m,4H), 7.15(s,4H).

D. Diammonium [4-(3-oxo-4,4,4-trifluoro-butyl)phenyl]phosphate

A 25 mL one neck round bottom flask, fitted with argon inlet and magnetic stirrer was charged with 5.0 mL of dichloromethane, 140 mg(0.4 mM) of diethyl [4-(3-oxo-4,4,4-trifluorobutyl)phenyl]phosphate and 2.0 mL of bromotrimethylsilane. After stirring this mixture for 3 hours at ambient temperature, 10 mL of methanol was added and the volatile materials were removed under reduced pressure. The residue was dissolved in water and the pH adjusted to 7.3 with 1.0 N NaOH. The aqueous solution was extracted with ethyl ether and lyophilized to give 190 mg of a white solid. This material was dissolved in 10 mL of 30 mM NH4OAc buffer and purified by HPLC using system A. Yield of the product after lyophilization was 50 mg (37%). mp 235°-240° C. nmr(D2O)α1.90(m,2H), 2.56(m,2H), 4.65(s,DOH), 6.88(dd,4H)J=6, 82 Hz.

EXAMPLE II

1-Hydroxy-5,5-difluoro-8,8-dimethyl-4-nonanone

A. Ethyl 2,2-difluoro-5,5-dimethylhexanoate

A 100 mL three neck round bottom flask fitted with dropping funnel, argon inlet, ice bath, and magnetic stirrer was charged with 8.0 mL of dichloromethane and 2.21 g(20 mM) of ethyl 2-oxo-5,5-dimethylhexanoate. Diethylaminosulfur trifluoride, 2.11 g(13 mM), in 5 ml of dichloromethane was added to the reaction mixture over a 15 minute period and the mixture was stirred overnight at ambient temperature. The reaction mixture was partitioned between water and dichloromethane, the organic layer dried (anhydrous MgSO4), and the solvent removed under reduced pressure. The oil residue was distilled at 83°-88° C. at 20 mm to give 1.0 g(25%). nmr(CDCl3)—α0.95(s.9H), 1.40(m,.4H), 2.10(m,2H), 4.35(q,2H).

B. 2,3,4,5-Tetrahydro-2-oxo-3-[(5,5-di-methyl-2,2-difluoro-1-oxo)hexyl]furan A 25 mL three neck round bottom flask, fitted with drying tube, dropping funnel, heating mantle, and magnetic stirrer was charged with 0.24 g(5.0 mM) of sodium hydride in a 50% oil dispersion. The sodium hydride was washed with dry hexane (2×10 mL) and 5.0 mL of ethyl ether was added to the flask. A mixture of 5 drops of absolute ethanol and 5 mL of ether was slowly added to the sodium hydride suspension. After the evolution of hydrogen had stopped, a mixture of 1.0 g(5.0 mM) of ethyl 2,2-difluoro-5,5-dimethyl-hexanoate and 0.43 g(5.0 mM) of -butyrolactone in 5.0 mL of ethyl ether was added over a 20 minute period. The solution was refluxed for 3 hours and allowed to stir at ambient temperature overnight. The reaction mixture was partitioned with 1 N HCL, the organic layer washed with water (2×50 mL), dried (anhydrous MgSO4), and the solvent removed under reduced pressure. The oil residue, 0.88 g, was crystallized from a hexane:ethyl acetate mixture, 0.66 g (53%). nmr—(CDCl3)—α0.95(s,9H), 1.35(m,2H), 2.00(m,3H), 2.50(m,2H), 3.00(m1H), 4.25(m,1H), 4.5(m,1H).

C. 1-Hydroxy-5,5-difluoro-8,8-dimethyl-4-nonanone

A 10 mL one neck round bottom flask, fitted with argon inlet, magnetic stirrer, and reflux condenser was charged with 1.0 mL glacial acetic acid, 4 drops of concentrated HCl and 200 mg(0.81*mM) of 2,3,4,5-tetrahydro-2-oxo-3-(5,5-di-methyl-2,2-difluoro-1-oxohexyl) furan. The reaction mixture was heated at 110° C. overnight under a blanket of argon. The reaction was extracted with ethyl ether, and the ether was cross washed with water, dried (anhydrous MgSO4), and solvent removed under reduced pressure. The residue was chromatographed on a 10×60 mm silica gel column using a 9:1 hexane:ethyl acetate mixture to give a clear oil. nmr(CDCl3α—0.95(s,9H), 1.45(t,2H), 2.00(m,6H), 3.12(bs,1H), 4.15(m,1H)

EXAMPLE III

N,N-dimethyl-N-[2-(hydroxy)ethyl]-5,5,5-trifluoro-4-oxopentanaminium, hydroxide salt

A. 2,3,4,5-Tetrahydro-2-oxo-3-[(2,2,2-trifluoro-1,1-dihydroxy)ethyl]furan

A 3 L three neck round bottom flask, fitted with reflux condenser, dropping funnel, argon inlet, magnetic stirrer, and heating mantle was charged with 36 g(0.75 M) of a 50% oil dispersion of sodium hydride. The sodium hydride was washed (2×200 mL) with dry hexane and then suspended in 800 mL of ethyl ether and 22 mL of absolute ethanol A mixture of 60.2 g(0.7 M) of -butyrolactone and 99.4 g(0.7 M) of ethyl trifluoroacetate in 750 mL of ether was added to the suspension at a rate to keep the reaction at gentle reflux. The mixture was refluxed for an additional two hours and then stirred at ambient temperature overnight. The reaction was cooled in an ice bath and 1 N HCl (250 mL) was added. The organic layer was separated, washed with water (2×200 mL), dried (anhydrous MgSO4), and solvent removed under reduced pressure. The residue was crystallized from hexane:ethyl acetate to give 64.0 g (45.4%), mp—87°–90° C. nmr(DMSO-d6)—α2.33(m,2H), 3.09(t,1H)J=7 Hz, 4.20(m,2H), 7.00(s,1H), 7.52(s,1H).

B. Preparation of 1,1,1-trifluoro-5-hydroxy-2-pentanone

A 500 mL three neck round bottom flask, fitted with reflux condenser, heating mantle, and magnetic stirrer was charged with 61.5 g(0.31 M) of 2,3,4,5-tetrahydro-2-oxo-3-(2,2,2-trifluoro-1,1-dihyroxyethyl)furan, 6.4 mL of concentrated HCl, 10 mL of water, and 80 mL of acetic acid. The reaction mixture was heated at 125° C. overnight. An additional 3.0 mL of concentrated HCl and 5.0 mL of water was added and the reaction mixture was heated for an additional 10 hours. The reaction was partitioned between water and ethyl ether while the water layer was neutralized with solid sodium bicarbonate (100 g). The ether solution was washed with water (2×20 mL), dried (anhydrous MgSO4), and solvent removed under reduced pressure to give 60 g(45%) of a pale yellow oil. nmr(CDCl3)α—2.14m,4H), 4.03(m,1H), 4.20(m,1H).

C. 1,1,1-Trifluoro-5-bromo-2-pentanone

A 500 mL three neck round bottom flask, fitted with dropping funnel, magnetic stirrer, ice-salt bath, and argon inlet is charged with 125 mL of dry dimethylformamide, 29 g(35.7 mM) of trifluoro-5-hydroxy-2-pentanone. This mixture was cooled to −5° C. and 11.5 g(71.6 mM) of bromine was added dropwise over a two hour period. After stirring overnight at ambient temperature the reaction mixture was distilled through a 30 cm vigreaux column at 2.0 mm of pressure. Two fractions were collected; the first fraction from 27°–35° C. and the second fraction at 35°–70° C. The second fraction was partitioned between water and ethyl ether, the organic layer was washed with water (3×100 mL, dried (anhydrous MgSO4), and evaporated under reduced pressure at ambient temperature to give 40 g of a colorless oil mixture of dimethyl formamide, ether, and the desired product which was used in the next reaction without further purification.

D. N, N-dimethyl-5,5,5-trifluoro-4-oxopentanamine

A 500 mL three neck round bottom flask, fitted with dropping funnel, argon inlet, magnetic stirrer, and ice-salt bath was charged with 21.5 g(0.45 M) of anhydrous dimethylamine at −8° C. To this mixture was added 19.4 g(88.5 mM) of 1,1,1-trifluoro-5-bromo-2-pentanone in dimethyl formamide and ethyl ether dropwise at −10° C. The suspension was stirred for 2.5 hours at −10° C. The solvent was then decanted from the precipitate. The precipitate was washed with ethyl ether (3×200 mL), the organic layers were combined, washed with water (2×30 mL), dried (anhydrous MgSO4), and evaporated under reduced pressure to give 15.0 g(92%) of a pale yellow oil. nmr of HCl salt (CDCL3)α—1.89(s,4H), 2.90(s,6H), 3.21(t,2H).

E. N,N-dimethyl-N-[2-methoxy)ethyl]-5,5,5-trifluoro-4-oxopentanaminium, hydroxide salt A 25 mL one neck round bottom flask was charged with 2.95 g (21.2 mM) of 2-bromoethyl methyl ether, 0.33 g(1.77 mM) of N, N-dimethyl-(5,5,5-trifluoro-4-oxopentanamine) and 2.5 mL of dimethyl formamide and the mixture was stirred at ambient temperature for 3 days. Solvent was removed under reduced pressure and the amber oil was chromatographed on a Dowex-1 (15×200mm) column in the hydroxide form with 200 mL of water. The effluent from the column was lyophilized to yield 0.28 g(60%) of an amber oil which was the product as the hydroxide salt. nmr(D2O)-—α1.94(m,2H), 3.13(s,6H), 3.39(s,3H), 3.41(m,2H), 3.60(m,2H), 3.88(bs,2H). The material was used in next reaction without further purification.

F. N,N-dimethyl-N-[2-hydroxy)ethyl]-5,5,5-trifluoro-4-oxopentanaminium, hydroxide salt A 10 mL round bottom flask, fitted with argon inlet and reflux condenser was charged with 0.275 g(1.1 mM) of N,N-dimethyl-N-[2-(methoxy)ethyl]-5,5,5-trifluoro-4-oxopentanaminium, hydroxide salt, 4.0 mL of water and 8.0 mL of 30% HBr in acetic acid. This mixture was heated at 120° C. for five hours, cooled, and the solvent removed under reduced pressure. The residue was co-evaporated with 3×20 mL of water and the resulting oil was chromatographed on a Dowex-1 (15×200 mm) column in the hydroxide form. Evaporation of the effluent under reduced pressure gave 0.17 g(63%) of the product as the hydroxide salt. nmr(D2O)-—α1.90(m,4H), 3.13(s,6H), 3.30(m,2H), 3 48(m,2H), 4.01(bs,2H).

EXAMPLE IV

N,N-dimethyl-N-[2-(phosphonooxy)ethyl]-5,5,5-trifluoro-4-oxopentanaminium, ammonium salt A 10 mL three neck round bottom flask fitted with dropping funnel, argon inlet, magnetic stirrer, and ice salt bath was charged with 0.093 mL(1.0 mM) of phosphorus oxychloride and 0.5 mL of trimethyl phosphate. To this mixture was added 70.0 mg(0.2 mM) of N,N-dimethyl-N-[2-(hydroxy)ethyl]-5,5,5-trifluoro-4-oxopentanaminium, hydroxide salt dropwise at −10° C. The mixture was stirred for 30 minutes and then placed in a freezer overnight. The mixture was triturated with ethyl ether followed by petroleum ether (4×50 mL) to give a resinous precipitate. This precipitate was covered with ice, neutralized to pH 6.0 with 1N NaOH, and evaporated to dryness under reduced pressure. The resulting solid, 107 mg, was dissolved in 30 mM NH4OAc buffer at pH 7.0 and purified by HPLC with system B. The product, which eluted at 12 minutes, was isolated by lyophilization of the buffer to give 9.0 mg(11%) of a colorless resin. nmr(D2O)−α1.90(m,4H, 3.14(s,6H), 3.42(m,2H), 3.60(m,2H), 4.19(bs,2H).

EXAMPLES V–VIII

Materials:
Ovalbumin
Buffer A: 50 mM potassium phosphate and 1 mM magnesium chloride, pH 7.3

Buffer B: 50 mM diethanolamine and 0.5 mM magnesium chloride, pH 9.0
Buffer C: 50 mM tris HCl, pH 8.0
β-gal., $2.3 \times 10^{-2}$ mg/Ml in Buffer A
AP, 0.4 mg/ML in Buffer B
−C, $7.0 \times 10^{-3}$ mg/ML in Buffer C
4-(4-(β-galactopyranosyl) phenyl 1,1,1-trifluoro-2-butanone, 300 μM in Buffer A (blocked inhibitor 1)
4-(4-(N-acetylphenylalanylamido)phenyl)-1,1,1-trifluoro-2-butanone, 100 mM in Buffer C (blocked inhibitor 2)
4-(4-phosphophenyl)-1,1,1-trifluoro-2-butanone, 300 mM in Buffer B (blocked inhibitor 3)
Dichloroindophenyl butyrate, 200 um in 50 mM Tris.

EXAMPLE V

Detection of β-galactosidase activity

A solution containing $1 \times 10^{-3}$ mg/ML of RLE and 0.2 mg/ML of ovalbumin was prepared in buffer A. A 0.9 ML aliquot was transferred to a plastic tube (tube 1), and 0.8 ML aliquots were transferred to an additional 10 tubes (tubes 2–11). β-Gal. in buffer A (100 μL) was added to tube 1, and 1:5 serial dilutions of this solution were made into tubes 2–10. Aliquots (50 μl) of the solutions in tubes 1–11 were transferred to the wells of a microtiter plate. To each well was added blocked inhibitor 1 (50 μL) followed 20 minutes later by 100 μL of substrate solution. Three minutes after addition of substrate, 25 μL of 1-propanol were added and the absorbance in each well at 620 nm was determined. The result of this experiment is shown in FIG. 1.

EXAMPLE VI

Detection of α-chymotrypsin activity

In the same way as described for Example V, α-C activity was determined by inhibition of color formation from substrate and RLE by the action of α-C on blocked inhibitor 2. The result of this experiment is shown in FIG. 1.

EXAMPLE VII

Detection of alkaline phosphatase activity

In the same way as described in Example V, AP activity was determined by inhibition of color formation from substrate and RLE by the action of AP on blocked inhibitor 2. The result of this experiment is shown in FIG. 1.

EXAMPLE VIII

Detection of β-galactosidase activity in urine

Figure 2:
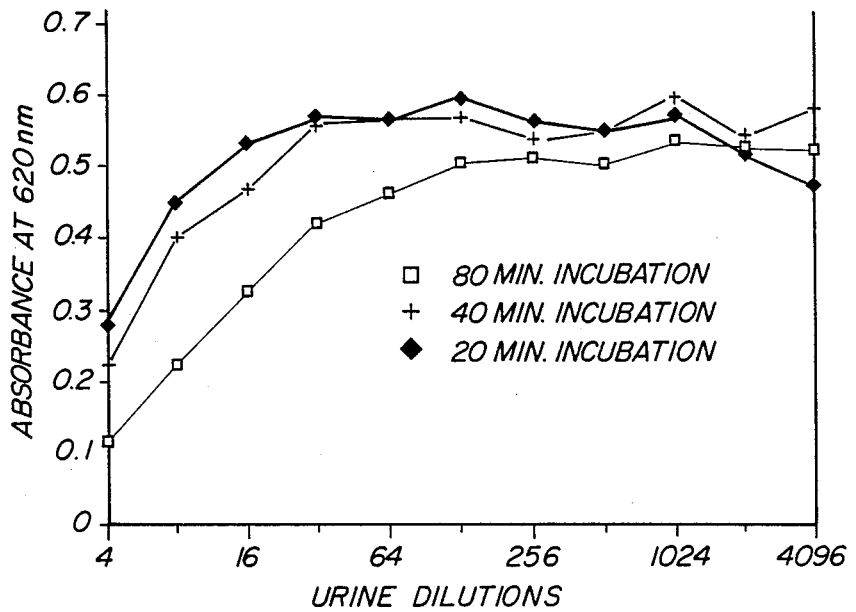
FIG. 2 shows application of the assay of the invention to detection of an enzyme in urine.

A solution containing $1 \times 10^{-3}$ mg/ml of RLE and 0.2 mg/mL of ovalbumin in Buffer A was divided (0.5 ml each) into 12 tubes. One mL of urine was mixed with 1 mL of buffer A, and 0.5 mL of this solution was serially diluted (1:2) into the 12 tubes. A 0.5 mL aliquot from each tube was transferred to the wells of 6 rows of a microtiter tray. At t=0 minutes (rows A and B), 40 minutes (rows D and E) and 60 minutes (rows G and H), 50 uL of a 300 uM solution of blocked inhibitor 1 in buffer A were added to wells 1–11. Column 12 received 50 uL of buffer A. At t=80 minutes, 100 uL of substrate solution were added to each well, followed 3 minutes later by 50 uL of 1-propanol. The absorbance in each well at 620 nm was determined. The results of this experiment are shown in FIG. 2.

In summary, the invention provides a method for detection or determination of an unknown enzyme present in a liquid. The liquid is contacted with a second enzyme and a blocked modulator whereby the unknown enzyme removes the blocking group to provide a modulator for the second enzyme. A substrate for the second enzyme is added. The modulator modulates conversion of the substrate to a product by the second enzyme, leading to a detectable signal. Detection of the signal establishes the presence or absence of the unknown enzyme sample. By measuring the magnitude of the signal, the concentration of the enzyme may be determined. The modulator and the second enzyme provide two amplification stages whereby the signal is amplified by 100 fold or more, enabling naked eye detection of the signal in a time up to 100 fold less than by conventional enzyme assay.

What is claimed is:

1. A method for determining an enzyme in a liquid comprising:
   (a) combining a liquid suspected of containing an unknown enzyme with a second enzyme and a blocked fluoroketone inhibitor of said second enzyme, said unknown enzyme hydrolyzing said blocked fluoroketone inhibitor to a fluoroketone inhibitor;
   (b) adding a substrate for said second enzyme, said fluoroketone inhibitor inhibiting hydrolysis of said substrate to a colored product by said second enzyme; and
   (c) determining said unknown enzyme by detecting a signal associated with said colored product.

2. The method in accordance with claim 1 further comprising determining the concentration of said unknown enzyme in said liquid by measuring the magnitude of said signal and comparing said magnitude with the magnitude of a signal associated with a product when steps (a) to (c) are repeated with a liquid sample containing a predetermined quantity of said unknown enzyme.

3. The method in accordance with claim 1 wherein said unknown enzyme is a hydrolase.

4. The method in accordance with claim 3 wherein said hydrolase is selected from the group consisting of a peptidase, esterase phosphatase, glycosidase, sulphatase, amidase, protease and β-lactamase.

5. The method in accordance with claim 4 wherein said phosphatase is selected from the group consisting of alkaline phosphatase and acid phosphatase.

6. The method in accordance with claim 4 wherein said glycosidase is selected from the group consisting of β-glucuronidase and β-galactosidase.

7. The method in accordance with claim 1 wherein said second enzyme is a hydrolase.

8. The method in accordance with claim 7 wherein said hydrolase is selected from the group consisting of an esterase, a phosphatase and a peptidase.

9. The method in accordance with claim 8 wherein said hydrolase is selected from the group consisting of acetylcholinesterase, butylcholin-esterase, carboxyesterase, trypsin, chymotrypsin and pepsin.

10. The method in accordance with claim 1 wherein said substrate is selected from the group consisting of an ester of a nitrophenol, and an ester of indoxyl.

11. The method in accordance with claim 1 wherein said step of detecting a signal includes detecting a color associated with said substrate.

12. The method in accordance with claim 1 wherein said step of detecting a signal includes detecting a color associated with said product.

13. A method for determining an enzyme in a liquid comprising:
   (a) combining a first liquid suspected of containing an unknown enzyme with an esterase and a blocked fluoroketone inhibitor of said esterase, said unknown enzyme hydrolyzing said blocked fluoroketone inhibitor to a fluoroketone inhibitor;
   (b) adding a chromogen, said fluoroketone inhibitor inhibiting the hydrolysis of said chromogen to a colored product by said esterase;
   (c) measuring the magnitude of said inhibiting; and
   (d) determining the concentration of said unknown enzyme in said liquid by comparing said magnitude with the magnitude of inhibition of formation of a colored product when steps (a) to (c) are repeated with a liquid sample containing a predetermined quantity of said unknown enzyme.

14. The method in accordance with claim 13 wherein said magnitude of inhibiting is an increase in the time until said colored product is detected in said liquid.

15. The method in accordance with claim 13 wherein said magnitude of inhibiting is a decrease in the color developed after a predetermined time.

16. A kit of materials for performing an assay for an unknown enzyme comprising a liquid containing a predetermined quantity of an unknown enzyme, a second enzyme, a substrate for said second enzyme and a blocked fluoroketone inhibitor of said second enzyme.

17. The kit of claim 16 further comprising a solution useful in performing said assay.

18. The kit of claim 17 wherein said solution is selected from the group consistent of a buffer and saline.

19. The kit in accordance with claim 16 further comprising a fluid sample substantially free of said unknown enzyme.

20. The kit in accordance with claim 16 further comprising one or more containers.

* * * * *